United States Patent [19]

Hart

[11] Patent Number: 4,759,875
[45] Date of Patent: Jul. 26, 1988

[54] OXO-DERIVED MILD SURFACTANT BLENDS

[75] Inventor: Gerald L. Hart, Surbiton, England

[73] Assignee: S. C. Johnson & Son, Inc., Racine, Wis.

[21] Appl. No.: 818,842

[22] Filed: Jan. 14, 1986

[51] Int. Cl.$^4$ .................. C11D 1/06; C11D 1/37; A61K 7/06; A61K 7/48
[52] U.S. Cl. ................. 252/551; 252/174.21; 252/557; 252/DIG. 5; 252/DIG. 13; 252/DIG. 14
[58] Field of Search ............ 252/551, 557, 174.21, 252/DIG. 5, DIG. 13, DIG. 14

[56] References Cited

U.S. PATENT DOCUMENTS

| | | | |
|---|---|---|---|
| 2,999,069 | 9/1961 | Masei et al. | 252/152 |
| 3,055,836 | 9/1962 | Masei et al. | 252/152 |
| 3,928,251 | 12/1975 | Bolich et al. | 252/152 |
| 4,223,163 | 9/1980 | Guilloty | 568/618 |
| 4,426,310 | 1/1984 | Verunica | 252/106 |

FOREIGN PATENT DOCUMENTS 0177071 4/1986 European Pat. Off. .
8402578 9/1986 Netherlands .
874186 8/1961 United Kingdom .

OTHER PUBLICATIONS

M. A. Esposito, et al., 37 Carboxylated Surfactants in Shampoos and Hair Care Formulations", *Cosmetics and Toiletries*, East Hanover, N.J., vol. 96, Jul., 1981, pp. 99–101.
J. Am. Acad. Derm., vol. 1, No. 1 (1979), 35:41.
McCutcheon's Emulsifiers and Detergents, 1981 International Editions, pp. 8, 229, 231.
Chem-4 Manufactures Literature on Akypo Tradename.

*Primary Examiner*—Paul Lieberman
*Assistant Examiner*—Linda D. Skaling

[57] ABSTRACT

A mild anionic surfactant blend for use in personal care compositions comprising oxo-derived anionic surfactants, fatty ether carboxylate and a fatty ether sulfosuccinate.

6 Claims, No Drawings

OXO-DERIVED MILD SURFACTANT BLENDS

BACKGROUND OF THE INVENTION

1. Field of the Invention

This invention relates to oxo-derived fatty sulphate or fatty ether sulphates in mild surfactant blends. Primarily these are anionic surfactants derived from alcohols prepared by an oxo-process. The surfactants include lauryl sulphate or lauryl ether sulphate, ether carboxylate, and lauryl ether sulphosuccinate.

2. Prior Art

Natural and synthetically derived anionic surfactants are old and well-known in the art. Indeed, compositions containing the reaction products of ethoxylated anionic surfactants and certain specific amphoteric surfactants and polyethoxylated nonionic surfactants have been disclosed in U.S. Pat. Nos. 2,999,069 and 3,055,836. Maskey and Poirier, respectively. In addition, carboxylated surfactants in shampoo and hair care formulations are also disclosed in the article *Cosmetic and Toiletries,* Page 99, by M. A. Esposito, K. F. Shoney, and B. A. Shukowsky, East Hanover, N.J., Volume 96, July 1981. The carboxylated surfactants of this article are effective surfactants. As detergents, their surface tension lowering properties are the same order and magnitude as more common anionics and it can be demonstrated that these carboxylates retain their surface active properties over a wide pH range. In their role as lime soap dispersants, the alkyl carboxylates perform to a degree that seems to have pushed the standard methodology to the limit. Findings on commercial products, as well as some new laboratory products, show as a class the carboxylates as effective LSD's in the range of 5% or less.

The Esposito article differs from the present invention in that the carboxylated surfactants of Esposito are seen for use in cationic systems. No discussion is had of combining them with other surfactants to provide the mild anionic surfactant blend of the present composition which is useful in substituting the less expensive synthetic versions of naturally derived surfactants. Accordingly, the present invention differs from and is not obvious in view of the Esposito article.

Combinations of sulphates, or ether sulphates with ether carboxylates have been disclosed, especially for shampoos, in GB-A-874.186, wherein it has been shown that this kind of composition possesses various synergistic actions. In NL-A-8402578 it has been shown that already at low percentages of ether carboxylate a large effect on the tolerance for hair and skin is obtained. These do not refer to the current invention which specifically embraces OXO-derived (ether) sulphates.

Bolich et al., U.S. Pat. No. 3,928,251, depicts a mild shampoo composition comprising specific ethoxylated anionic surfactants with specific Zwitterionic surfactants and polyethoxylated nonionic surfactants. Bolich differs from the present invention in that the fatty ether carboxylates, and specifically, the sodium laureth N-carboxylate surfactant, is not included in a mix as to make the composition unexpectedly mild and function well in anionic systems. Accordingly, the present invention differs from and is an improvement over Bolich.

SUMMARY OF THE INVENTION

The present invention is a mild surfactant blend incorporating fatty (ether) sulphates derived from oxo-alcohols and is useful in mild shampoos and soap compositions. The anionic surfactants derived from alcohols prepared from the oxo-processes are usually more irritating to skin than natural-based surfactants. The present invention allows the more aggressive oxo-based surfactants to be used in personal toiletries without any increases in primary skin irritation as compared to natural based surfactants. This is achieved by incorporating the oxo-surfactant in a blend where two other surfactants are present. These other surfactants are lauryl ether carboxylate with ethoxylation greater than 2 moles and disodium lauryl ether sulphosuccinate with ethoxylaton of 2 to 3 moles. The lauryl ether carboxylates, in combination with the oxo-based (ether) sulphates give rise to the superior synthetic surfactant blend which is of a reduced cost as compared to the naturally occurring surfactant and does not, as would be expected, increase irritation factors. The combination of the carboxylates with the sulphosuccinate further improves the mildness and foaming texture of the compositions formed according to the present invention. Accordingly, the present invention is a three component system; (1) an oxo-derived (ether) sulfate; (2) a lauryl ether carboxylate; and (3) a lauryl ether sulphosuccinate.

Accordingly, it is an object of the present invention to provide a mild oxo-derived surfactant blend which has carbon number distributions emcompassing $C_{10}$, $C_{11}$, $C_{12}$, $C_{13}$, $C_{14}$, $C_{15}$, $C_{16}$, which has the same irritation factors as a naturally derived anionic surfactant covering $C_{10}$, $C_{12}$, $C_{14}$, $C_{16}$.

It is a further object of this invention to combine the surfactant together and incorporate them into personal toiletries to produce products which have reduced skin irritation and eye irritations as compared with other personal toiletries having synthetic surfactants and not utilizing the surfactant blends of the present invention.

DETAILED DESCRIPTION OF THE PREFERRED EMBODIMENT

The present invention is a surfactant blend comprising an anionic surfactant derived from fatty alcohols by an oxo-process. The oxo-derived anionic surfactants are usually more irritating to skin and eyes than naturally-based surfactants such as those derived from coconut oils. However, certain advantages may be seen with utilization of synthetic equivalents of naturally-derived surfactants. These include consistency of supply, ease of manufacture, and the fact that they are frequently cheaper to use than naturally-derived compounds. In recent years, it has become increasingly critical, due to the fluctuations in the commodities market, to find a substitute for naturally derived surfactants based on coconut oil.

The surfactant blend of the present invention is basically an anionic surfactant blend having a carbon content range of primarily $C_{10}$, $C_{11}$, $C_{12}$, $C_{13}$, $C_{14}$, $C_{15}$, and $C_{16}$. This invention allows the more aggressive oxo-derived anionic surfactants to be used in personal toiletries without any increase in the primary skin irritation as compared to natural-based types. This aim is achieved by incorporating the surfactant in a blend with at least two other surfactants. These surfactants include sodium lauryl ether carboxylate with ethoxylation greater than 2 moles, and di-sodium lauryl ether sulphosuccinate with ethoxylation of 2 to 3 moles. The combination of the oxo-base surfactant with the sulphosuccinate further improves the mildness and foaming textures of the resulting product. Accordingly, the present invention comprises a three component system; namely, a basic anionic surfactant, a lauryl ether carboxylate and a lauryl ether sulphosuccinate.

The basic anionic surfactants are fatty alcohol sulphates and fatty alcohol ether sulphates based on synthetic alcohols prepared by the aforementioned oxo-process which is old and well known in the art. The synthetic alcohols typically have a carbon number distribution encompassing $C_{10}$, $C_{11}$, $C_{12}$, $C_{13}$, $C_{14}$, $C_{15}$, and $C_{16}$ and with up to about 50% chain branching. These are ethoxylated with about up to 4.0 moles of ethylene oxide per mole of alcohol and after sulphation and neutralization with sodium, will have a molecular weight ranging from about 340 to 460. Although sodium is the preferred ion to be incorporated with the ethoxylated fatty alcohol ether sulphate, other ions may be used instead of sodium, including magnesium, ammonium, alkanolamine and the like.

The anionic surfactants conform to the general structure:

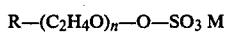

wherein R is a lipophilic group consisting of alkyl groups containing from about 10 to about 16 odd and even numbers of carbon atoms, n is a number from 0 to 10 and M is a nontoxic cation which makes the surfactant water soluble.

The fatty ether carboxylate portion of the surfactant blends may be either natural or synthetic The fatty ether carboxylate surfactant is ethoxylated from a range of about 2 moles ethylene oxide per mole to about 25 moles ethylene oxide per mole. The fatty ether carboxylic acid may be neutralized with a variety of counterions selected from the group consisting of sodium, magnesium, ammonium, alkanolamine, and the like. The carboxylic surfactants conform to the general structure

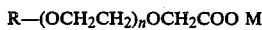

where R is in principle, any alkyl group, alkyl phenyl, etc., having a carbon content of C10 to C18, n is any number greater than 2, and M is a non toxic cation which makes the surfactant water soluble. The most common forms and the most readily available commercial products are the ethoxylated fatty alcohols. Alkoxylated alkyl carboxylates of other residues also show great promise and have significant uses in various applications. However, the fatty alcohol-derived carboxylates represent the clearly dominant position in carboxylate usage in personal care products and, as such, ase the preferred carboxylates of the present invention.

Carboxylated fatty alcohols are very effective surfactants. As detergents, their surface tension lowering properties are of the same order of magnitude as more common anionics and it can be demonstrated that these carboxylates retain their surface active properties over wide pH range. As emulsifiers, the apparent transition from salt to acid form, i.e., from anionic to nonionic function, is a function of pH and renders certain of the group effective as variable HLB surfactants so that emulsions formed with these compounds can be easily thinned, thickened, even inverted through pH adjustment. Carboxylated acids currently find great usefulness as cosurfactants in mixed surfactant systems. Apparently, the inclusion of the fatty ether carboxylate portion of the surfactant decreases the naturally aggressive tendency of the oxo-derived anionic surfactants.

The fatty ether sulphosuccinate portion of these surfactants may be natural or synthetic. Ethoxylation ranges from about 2 to 3 moles of ethylene oxide per mole of sulphosuccinate. The fatty ether sulphosuccinate is usually sold as sodium salts from solubility considerations. The fatty ether sulphosuccinates are those sulphosuccinates having the formula;

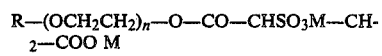

wherein R is a hydrocarbon residue or mixture of hydrocarbon residues of primarily 10 to 16 carbon atoms and n is from 2 to 3 and M is a non toxic cation which makes the surfactant water soluble.

The basic anionic surfactant, fatty ether carboxylates and sulphosuccinates are blended together to form a product having a pH of about 4 to about 8 with active ratio of basic anionic surfactant to fatty ether carboxylate of between 5:1 and 1:1 and an active ratio of fatty ether carboxylate to fatty ether sulphosuccinate of between 10:1 and 1:1.

In the preferred embodiment, the oxo-derived surfactant is present in an amount of about 8% to 25% by weight of the composition, the fatty ether carboxylate surfactant is present in an amount of about 12% to about 2% by weight of the composition, the fatty ether sulfosuccinate is present in an amount of about 0.5 to about 6.5% by weight of the composition, and the balance of the composition being water.

It is contemplated that the anionic surfactant blends of this invention are necessarily mild. It is essential that the anionic surfactant blends be mild since the oxo-derived surfactant is normally a more irritating surfactant than other synthetic or naturaly derived surfactants. The anionic surfactants provide good lathering properties. Typically, the composition will contain from about 10% to about 30% of active anionic surfactant, preferably, from about 13% to about 18% actives for a liquid shampoo, and from about 10% to about 15% actives for a hand soap.

The following are examples of various anionic shampoo and hand cleansing products made incorporating the surfactant blend of the present invention, and are not intended to limit the scope or spirit of the invention. The oxyethylene units have been abbreviated to "EO".

EXAMPLE 1

SYNTHETIC 'LIQUID' SOAP

Sodium Lauryl Ether (2 EO) Sulphate (28%): 45.00%
Sodium Lauryl Ether (10 EO) Carboxylate (90%): 6.20%
Di-Sodium Lauryl Ether (3 EO) Sulphosuccinate (40%): 1.80%
Pearl Concentrate: 4.00%
Water: -[100.00%

EXAMPLE 2

SHOWER GEL

Triethanolamine Lauryl Ether (2 EO) Sulphate (40%): 74.00% Triethanolamine Lauryl Ether (6 EO) Carboxylate (90%): 7.20%
Di-Sodium Lauryl Ether (3 EO) Sulphosuccinate (40%): 2.50%
Water: -[100.00%

EXAMPLE 3

BATH FOAM

Ammonium Lauryl Ether (1 EO) Sulphate (28%): 42.00%
Ammonium Lauryl Ether (3.8 EO) Carboxylate (90%): 4.00%
Di-Sodium Lauryl Ether (3 EO) Sulphosuccinate (40%): 6.50%
Water: –[100.00%

EXAMPLE 4

SHAMPOO

Triethanolamine Lauryl Ether (2 EO) Sulphate (40%): 51.20%
Triethanolamine Lauryl Ether (3.8 EO) Carboxylate (90%): 5.40%
Di-Sodium Lauryl Ether (3 EO) Sulphosuccinate (40%): 4.00%
Water: –[100.00%

EXAMPLE 5

CONDITIONING SHAMPOO

Sodium Lauryl Ether (2 EO) Sulphate (30%): 50.00%
Sodium Lauryl Ether (3.8 EO) Carboxylate (90%): 7.40%
Di-Sodium Lauryl Ether (3 EO) Sulphosuccinate (40%): 2.50%
Quaternium - 22: 2.00%
Water: –[100.00%

EXAMPLE 6

BABY SHAMPOO

Magnesium Lauryl Ether (2 EO) Sulphate (30%): 35.20%
Magnesium Lauryl Ether (16 EO) Carboxylate (90%): 5.90%
Di-Sodium Lauryl Ether (3 EO) Sulphosuccinate (40%): 2.80%
Water: –[100.00%

I claim:

1. A mild cleansing composition comprising surfactants and water, said surfactants consisting of a mixture of:

A. An oxo-derived surfactant selected from active sulphate and ether sulphate having a carbon content of primarily C10 to C16 and having the formula:

$$R-(C_2H_4O)_n-O-SO_3 M$$

wherein R is a lipophilic group consisting of alkyl groups containing from about 10 to about 16 odd and even numbers of carbon atoms, said lipophilic group having up to about 50% chain branching atoms, wherein n is a number from 0 to 10, and M is a nontoxic cation which makes the surfactant water soluble, said anionic surfactant having a molecular weight of from about 340 to about 460:

B. A fatty ether carboxylate surfactant having the formula:

$$R-(OCH_2CH_2)_n-OCH_2COO\ M$$

wherein R is an alkyl or alkyl phenyl group having a carbon content of primarily C10 to C18, n is a number greater than 2, and M is a nontoxic cation which makes the surfactant water soluble, said fatty ether carboxylated surfactant being ethoxylated from a range of about 2 moles to about 25 moles ethylene oxide per mole of surfactant, and;

C. A fatty ether sulfosuccinate having the formula:

$$R-(OCH_2CH_2)_n-O-CO-CH-SO_3M-CH_2-COO\ M$$

wherein R is a hydrocarbon residue or mixture of hydrocarbon residues having a carbon content of primarily C10 - C16, n is a number from 2 to 3, and M is a nontoxic cation which makes the surfactant water soluble, the molecular ratio of (A) to (B) is from about 5:1 to 1:1 and the molecular ratio of (B) to (C) is from about 10:1 to 1:1.

2. The composition of claim 1 wherein the oxo-derived surfactant is ether sulphate present in an amount of from about 8% to about 25% by weight of the composition.

3. The composition of claim 1 wherein the fatty ether carboxylate surfactant is present in an amount of from about 12% to about 2% active substance by weight of the composition.

4. The composition of claim 1, wherein the fatty ether sulfosuccinate is present in an amount of from about 0.5% to about 6.5% active substance by weight of the composition.

5. The composition of claim 1, wherein the pH is between 4 and 8.

6. The composition of claim 1 wherein the nontoxic cations are selected from the group consisting of alkali metal or alkaline earth metal, ammonium or substituted ammonium cations and mixtures thereof.

* * * * *